United States Patent [19]
Heller et al.

[11] Patent Number: 5,944,933
[45] Date of Patent: Aug. 31, 1999

[54] METHOD FOR DISTRIBUTING MOLECULAR SIEVE POWDER

[75] Inventors: Harold Norbert Heller, Menasha, Wis.; Ellyn Louise Conger, Moore, S.C.; Steven Wayne Fitting, Acworth, Ga.

[73] Assignee: Kimberly-Clark Worldwide, Inc., Neenah, Wis.

[21] Appl. No.: 08/870,622

[22] Filed: Jun. 6, 1997

Related U.S. Application Data

[60] Provisional application No. 60/020,328, Jun. 24, 1996.

[51] Int. Cl.⁶ .............................. B32B 31/12; B01J 20/18; C01B 39/02; A61L 15/18
[52] U.S. Cl. ........................ 156/276; 156/324; 604/359; 604/367; 502/64; 423/717; 427/190; 427/205
[58] Field of Search ................................... 156/276, 324; 264/69, 118; 604/359, 360, 367; 502/64; 423/716, 717; 427/180, 202, 205, 190

[56] References Cited

U.S. PATENT DOCUMENTS

| | | | |
|---|---|---|---|
| 3,340,875 | 9/1967 | Dudley et al. | 128/290 |
| 3,509,254 | 4/1970 | Krotinger, Jr. et al. | 424/76 |
| 3,903,259 | 9/1975 | Hart | 424/76 |
| 4,289,513 | 9/1981 | Brownhill et al. | 55/387 |
| 4,296,166 | 10/1981 | Ogino | 428/283 |
| 4,333,857 | 6/1982 | Lim et al. | |
| 4,388,075 | 6/1983 | Mesek et al. | 604/385 |
| 4,414,130 | 11/1983 | Cheng | |
| 4,525,410 | 6/1985 | Hagiwara et al. | 428/198 |
| 4,699,823 | 10/1987 | Kellenberger et al. | 428/219 |
| 4,748,065 | 5/1988 | Tanikella | 428/152 |
| 4,795,482 | 1/1989 | Gioffre et al. | 55/75 |
| 4,816,220 | 3/1989 | Roychowdhury | 422/5 |
| 4,826,497 | 5/1989 | Marcus et al. | 604/359 |
| 4,855,154 | 8/1989 | Gioffre et al. | 426/417 |
| 4,938,754 | 7/1990 | Mesek | 604/385.2 |
| 5,013,335 | 5/1991 | Marcus | 55/70 |
| 5,019,062 | 5/1991 | Ryan et al. | 604/359 |
| 5,037,412 | 8/1991 | Tanzer et al. | 604/359 |
| 5,084,427 | 1/1992 | Tsoucalas | 502/62 |

(List continued on next page.)

FOREIGN PATENT DOCUMENTS

| | | |
|---|---|---|
| 0 347 746 B1 | 12/1989 | European Pat. Off. |
| 0 389 023 A2 | 9/1990 | European Pat. Off. |
| 0 483 428 A1 | 5/1992 | European Pat. Off. |
| 0 506 282 A1 | 9/1992 | European Pat. Off. |
| 0 513 933 A1 | 11/1992 | European Pat. Off. |
| 0 731 059 A1 | 9/1996 | European Pat. Off. |
| WO 91/11977 A1 | 8/1991 | WIPO |
| WO 91/12029 A1 | 8/1991 | WIPO |
| WO 91/12030 A1 | 8/1991 | WIPO |
| WO 94/22501 A1 | 10/1994 | WIPO |

OTHER PUBLICATIONS

"Molecular Sieves," *Encyclopedia of Chemical Technology*, vol. 16, 4$^{th}$ Edition, 1995, pp. 888–925.

"Molecular Sieve," *Encyclopedia of Science & Technology*, vol. 11, 7$^{th}$ Edition, 1992, pp. 357–358.

"Zeolite," *Encyclopedia of Science & Technology*, vol. 19, 7th Ed. 1992, pp. 619–620.

Breck, D.W. and John Wiley & Sons, "Zeolite Molecular Sieves—Structure, Chemistry, and Use," 1974, pp. 245–250, 313–314, and 348–352.

Occelli, M.L. and H.E. Robson, "Zeolite Synthesis," ACS Symposium Series 398, 1989, pp. 2–7.

*Primary Examiner*—Curtis Mayes
*Attorney, Agent, or Firm*—Patricia A. Charlier

[57] ABSTRACT

A method for distributing a zeolite, including molecular sieve, powder having a median particle size of less than about 350 microns includes controlling the moisture content of the zeolite particles to greater than about 3 percent and thereafter refining the powder to reduce the size of agglomerated clusters.

66 Claims, 4 Drawing Sheets

U.S. PATENT DOCUMENTS

| | | | |
|---|---|---|---|
| 5,120,693 | 6/1992 | Connolly et al. | 502/64 |
| 5,124,177 | 6/1992 | Kasmark, Jr. et al. | 427/202 |
| 5,139,782 | 8/1992 | Jung | 424/401 |
| 5,147,343 | 9/1992 | Kellenberger | 604/368 |
| 5,152,972 | 10/1992 | Gier | 423/710 |
| 5,184,630 | 2/1993 | Jung | 132/202 |
| 5,192,277 | 3/1993 | Chung et al. | 604/360 |
| 5,192,606 | 3/1993 | Proxmire et al. | 428/284 |
| 5,254,337 | 10/1993 | Marcus et al. | 424/76.1 |
| 5,306,487 | 4/1994 | Karapasha et al. | 424/76.6 |
| 5,407,442 | 4/1995 | Karapasha | 604/359 |
| 5,429,628 | 7/1995 | Trinh et al. | 604/359 |
| 5,486,166 | 1/1996 | Bishop et al. | 604/366 |
| 5,490,846 | 2/1996 | Ellis et al. | 604/366 |
| 5,509,915 | 4/1996 | Hanson et al. | 604/378 |
| 5,704,556 | 1/1998 | McLaughlin . | |

METHOD FOR DISTRIBUTING MOLECULAR SIEVE POWDER

This application claims priority from U.S. Provisional Application No. 60/020,328 filed on Jun. 24, 1996.

BACKGROUND OF THE INVENTION

The present invention relates to a method for handling powderous materials comprising fine particulate. More particularly, the invention pertains a method for distributing a zeolite, such as a molecular sieve powder.

Zeolites, such as molecular sieves, have a crystalline structure that is particularly suited for adsorbing odorous materials. Zeolites are both naturally occurring and synthetically produced. Zeolites are inherently statically charged insulators that electrostatically attract the adsorbates. In addition to driving the absorptive forces, however, the static charge of zeolites, more specifically molecular sieves also lead to material handling difficulties. In the past, these difficulties have rendered the use of zeolites, including molecular sieves, uneconomical and/or problematic for many applications.

Static electricity causes zeolite powder to agglomerate during processing into relatively large, non-uniform clusters having substantial integrity. These clusters reduce the cost effectiveness of the final product and the performance efficiency of the zeolite by causing a very high degree of powder weight add-on variability and non-uniform deposition. Additionally, an unacceptably large amount of the statically charged particles tend to become airborne and contaminate the working environment. Due to their electrical charge, the zeolite particles cannot thereafter be easily removed from working surfaces by airjets or vacuum.

Previous attempts to manage the foregoing processing problems associated with zeolites have focused on increasing the particle size, either by increasing the size of the zeolite itself or by bonding the zeolite, such as a molecular sieve, to another substance. While increasing the particle size may lessen somewhat weight add-on variability and reduce deposition non-uniformity, this approach remains unsatisfactory. The larger zeolites or zeolite composites are cost prohibitive for many applications and do not significantly reduce airborne dust contamination.

Therefore, what is lacking and needed in the art is an economical approach to distributing zeolite, and more specifically molecular sieve, powders.

SUMMARY OF THE INVENTION

In response to the discussed deficiencies in the prior art, a new and economical approach to distributing zeolite, and more specifically molecular sieve, powders has been developed. In one embodiment, a method for distributing a zeolite powder includes the steps of: providing a powder comprising clusters of zeolite particles, which particles have a median particle size of less than about 350 microns; controlling the moisture content of the molecular sieve particles to greater than about 3 percent; and thereafter refining the powder to reduce the size of the clusters.

The refining is effective to reduce the size of powder clusters as a result of lower static levels obtained at the indicated moisture content. In particular embodiments, the moisture content is controlled to greater than about 4 percent, and particularly greater than about 7 percent. In the manufacture of absorbent articles, the moisture content is controlled in a range between about 6 and about 15 percent, particularly between about 7 and about 12 percent, and more particularly between about 8 and about 10 percent, such as about 9 percent, to reduce static and improve refining without degrading the effectiveness of the zeolite. The refining may be accomplished in a variety of ways, with particularly efficient methods including extruding and/or vibrating the powder. Powder clusters having a mean diameter of less than about 1500 microns, and particularly less than about 1100 microns, are believed to be particularly well suited for use in absorbent articles.

Thus, another aspect relates to a method for making an absorbent article. The method includes the steps of: providing a powder comprising clusters of zeolite, such as molecular sieve, particles, which particles have a median particle size of less than about 350 microns; controlling the moisture content of the zeolite particles to greater than about 3 percent; thereafter refining the powder to reduce the size of the clusters; providing a moisture barrier, a bodyside liner and an absorbent assembly; disposing the absorbent assembly between the moisture barrier and the bodyside liner; distributing the refined powder between the moisture barrier and the bodyside liner; and bonding the bodyside liner to the moisture barrier.

Numerous features and advantages of the present invention will appear from the following description. In the description, reference is made to the accompanying figures which illustrate preferred embodiments of the invention. Such embodiments do not represent the full scope of the invention. Reference should therefore be made to the claims herein for interpreting the full scope of the invention.

DETAILED DESCRIPTION OF THE PREFERRED EMBODIMENTS

Figure 1:
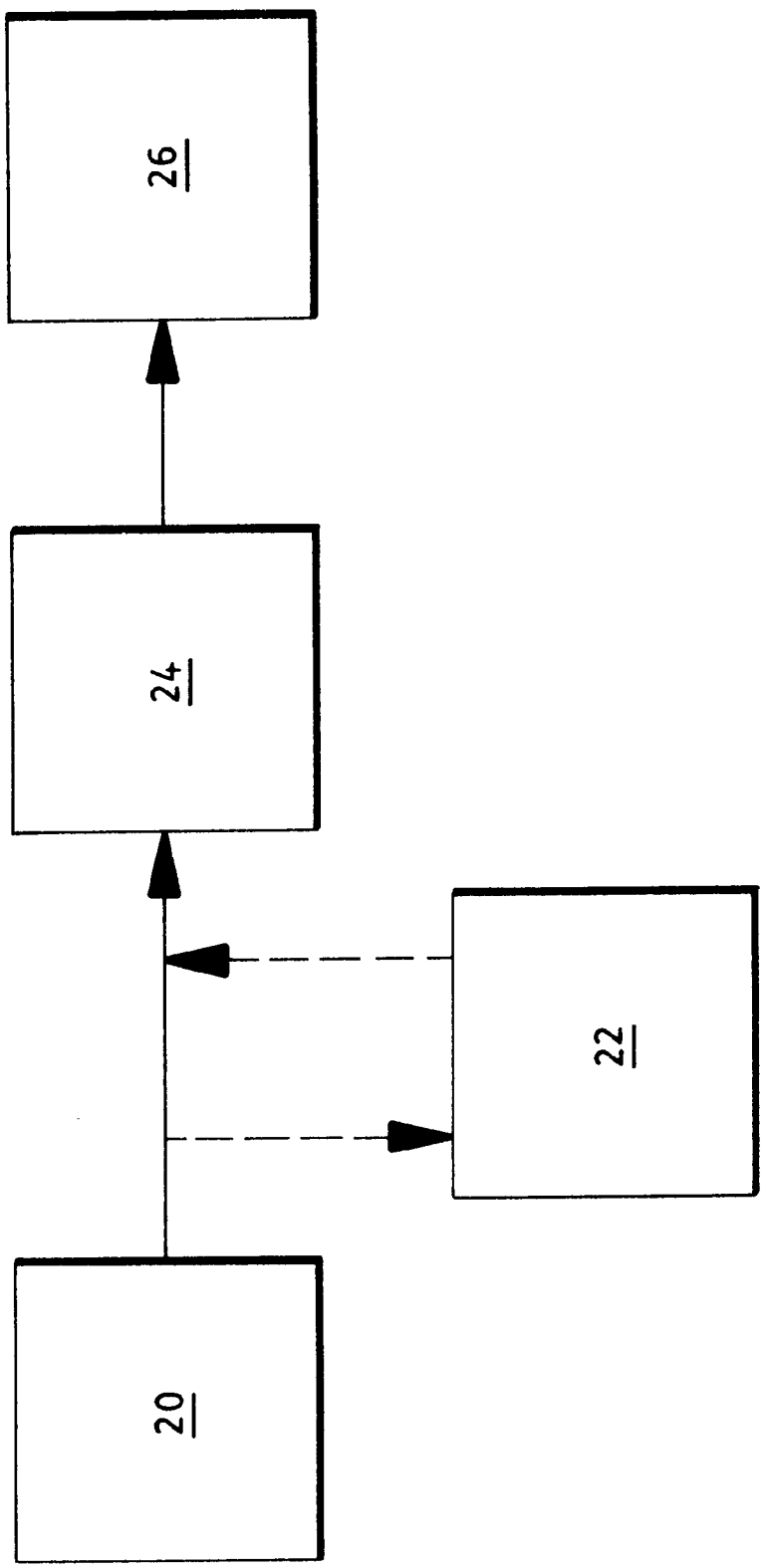
FIG. 1 representatively shows a schematic illustration of a method for processing a zeolite, such as molecular sieve, powder.

A method for distributing powderous materials comprising fine particulates such as zeolites is schematically illustrated in FIG. 1. The illustrated method distributes a zeolite (such as a bulk molecular sieve) powder onto a carrier (including carrier substrate) for eventual incorporation in an absorbent article. Alternatively, however, the method may be used to distribute the powder directly into a finished product. Further, the method pertains to the use of a zeolite in other types products such as tissues, wipers, medical garments, other absorbent articles such as diapers, training pants, feminine care products, other adult incontinence products, or the like.

A powder comprising zeolite particles is provided from a source 20 of zeolite powder. The moisture content of the zeolite particles is desirably controlled to greater than about 3 percent. The zeolite particles are desirably supplied from the source 20 with the desired moisture content. Alternatively, the powder may be routed to an optional moisture station 22 to raise or lower the moisture content of the zeolite powder to the desired level. The powder is thereafter processed at a refining station 24 to reduce the size of clusters of the zeolite particles. The term "clusters" is used herein to refer to agglomerations of zeolite particles which result in part from their static charge. The refined powder may then be distributed onto an intermediate carrier, carrier substrate, or directly into a finished product at a deposition station 26.

When entering the refining station 24, the zeolite particles desirably have a moisture content of greater than about 3 percent, particularly greater than about 4 percent, and more particularly greater than about 7 percent. In the manufacture of absorbent articles, the moisture content is controlled within a range of from about 6 to about 15 percent, particularly from about 7 to about 12 percent, and even more particularly from about 8 to about 10 percent, for improved handling and distribution.

For purposes of the present invention, the term "zeolite" refers to a microporous crystalline structure having pore diameters large enough to absorb at least one odorous organic molecular species, or compositions containing such structures. Such structures are both naturally occurring and synthetically produced. Such a structure is typically composed of primary structural units, $MO_4$, tetrahedra, combined into secondary structural units, such as a polyhedra. M is typically, although not necessarily for purposes hereof comprised at least one of aluminum, and/or silicon. M may also be comprised of sodium, magnesium, potassium, calcium, strontium, barium, titanium, zinc, iron, cobalt, and manganese.

A method for distributing powderous materials comprising fine particulates, specifically molecular sieves, is also schematically illustrated in FIG. 1. The illustrated method distributes a bulk molecular sieve powder onto a carrier (including carrier substrate) for eventual incorporation in an absorbent article. Alternatively, however, the method may be used to distribute the powder directly into a finished product. Further, the method pertains to the use of a molecular sieve in other types products such as tissues, wipers, medical garments, other absorbent articles such as diapers, training pants, feminine care products, other adult incontinence products, or the like.

A powder comprising molecular sieve particles is provided from a source 20 of molecular sieve powder. The moisture content of the molecular sieve particles is desirably controlled to greater than about 7 percent. The molecular sieve particles are desirably supplied from the source 20 with the desired moisture content. Alternatively, the powder may be routed to an optional moisture station 22 to raise or lower the moisture content of the molecular sieve powder to the desired level. The powder is thereafter processed at a refining station 24 to reduce the size of clusters of the molecular sieve particles. The term "clusters" is used herein to refer to agglomerations of molecular sieve particles which result in part from their static charge. The refined powder may then be distributed onto an intermediate carrier substrate or directly into a finished product at a deposition station 26.

When entering the refining station 24, the molecular sieve particles desirably have a moisture content of greater than about 3 percent, particularly greater than about 4 percent, and more particularly greater than about 7 percent. In the manufacture of absorbent articles, the moisture content is controlled within a range of from about 6 to about 15 percent, and even more particularly from about 8 to about 10 percent, for improved handling and distribution.

For purposes of the present invention, the term "molecular sieve" refers to a microporous crystalline structure having pore diameters large enough to adsorb at least one odorous organic molecular species, or compositions containing such structures. In its anhydrous form, such structure is typically composed of an orderly arrangement of corner-sharing $MO_2$ tetrahedra, in which "M" has historically although not necessarily for purposes hereof comprised at least one of aluminum and/or silicon.

One suitable procedure for determining the moisture content of zeolite (including molecular sieves) particles is a gravimetric procedure referred to as a loss on ignition test. The test includes heating a crucible in a muffle furnace for 1 hour at 1000 degrees Celsius; cooling the crucible in a desicator for 1 hour; recording the empty weight of the cooled crucible; placing approximately 1 gram of zeolite particles in the crucible; recording the initial combined weight of the crucible and particles; heating the crucible and particles in the muffle furnace for 1 hour at 1000 degrees Celsius; cooling the crucible and particles in the desicator for 1 hour; and recording the final combined weight of he crucible and particles. The initial combined weight minus the empty weight is the beginning weight of the zeolite particles. The final combined weight minus the empty weight is the ending weight of the particles. The moisture content of the zeolite particles is the beginning weight minus the ending weight, divided by the beginning weight and expressed as a percentage. An approximated value for the loss on ignition test can be determined using a moisture analyzer available for Sartorious AG Gottingen of Germany and identified as united MA-30.

Exemplary zeolite materials are disclosed in U.S. Pat. Nos. 4,795,482 issued Jan. 3, 1989, to Gioffre et al.; 4,826,497 issued May 2, 1989, to Marcus et al.; 5,013,335 issued May 7,1991, to Marcus; and, 5,152,972 issued Oct. 6, 1992, to Gier. ZEOLITE SYNTHESIS ACS Symposium Series 398, Eds. M. L. Occelli and H. E. Robson (1989) pgs 2–7; MOLECULAR SIEVES, Encyclopedia of Chemical Technology, Vol.16, pgs 888–925, 4th Ed. (1995); MOLECULAR SIEVE, Encyclopedia of Science & Technology, Vol. 11, pgs 357–358, 7th Ed. (1992); ZEOLITE, Encyclopedia of Science & Technology, Vol. 19, pgs 619-620, 7th Ed. (1992); ZEOLITE MOECULAR SIEVES, Structure, Chemistry and Use, by D. W. Breck, John Wiley & Sons (1974) pgs 245–250, 313-314 and 348–352.

Exemplary molecular sieve materials are disclosed in U.S. Pat. Nos. 4,795,482 issued Jan. 3, 1989, to Gioffre et al.; 4,826,497 issued May 2, 1989, to Marcus et al.; 5,013,335 issued May 7, 1991, to Marcus; and, 5,152,972 issued Oct. 6, 1992, to Gier; the disclosures of which are incorporated herein by reference. Molecular sieves for use with the present distribution method are available from commercial vendors such as UOP, which has offices in Des Plaines, Ill., USA. Particular molecular sieves from UOP include those referred to by the trademark ABSCENTS and the trade designation #3000 or #3318, although any other small particle size molecular sieve composition may be suitable as well.

The powder desirably comprises individual zeolite particles having a median particle size of less than 350 microns, particularly less than 200 microns, more particularly less than about 100 microns, and most particularly less than about 50 microns. In one particular embodiment, the zeolite has a particle size distribution from 1.4 to 44 microns with a median particle size of about 3.7 microns. One suitable procedure for determining the particle size of a zeolite is a standard sieve analysis, although other techniques such as optical microscopy, image analysis, optical or resistivity zone sensing, or the like may also be appropriate depending upon the general size of the particles. The procedure for measuring particle size takes into consideration individual zeolite particles or agglomerates of such particles.

Applicants have discovered that improved handling and distribution of zeolite particles is possible when the moisture content is controlled to relatively high levels. By controlling the moisture content of the zeolite particles to the indicated levels, the powder becomes conductive and thus discharges most of its static charge. This can be visually observed by a reduction in the occurrence of sparks that would otherwise be present, and by less movement of the particles as a consequence of objects, such as a person's hand, moving in close proximity to the particles. The reduced static levels diminish the propensity of the zeolite particles to form clusters and limit the integrity of the clusters to levels at which separation, for example by mechanical means, is economically feasible. More specifically, the powder can be separated into a finer and more uniform final particulate. This improved zeolite distribution permits a cost effective utilization of the odor control material because the finer distribution provides better odor adsorption performance. From a processing standpoint, the reduced levels of static also lessen airborne contamination, referred to as dusting; decrease buildup of the material on working surfaces; and permit easier removal of any such buildups by airjets or vacuum.

Figure 2:
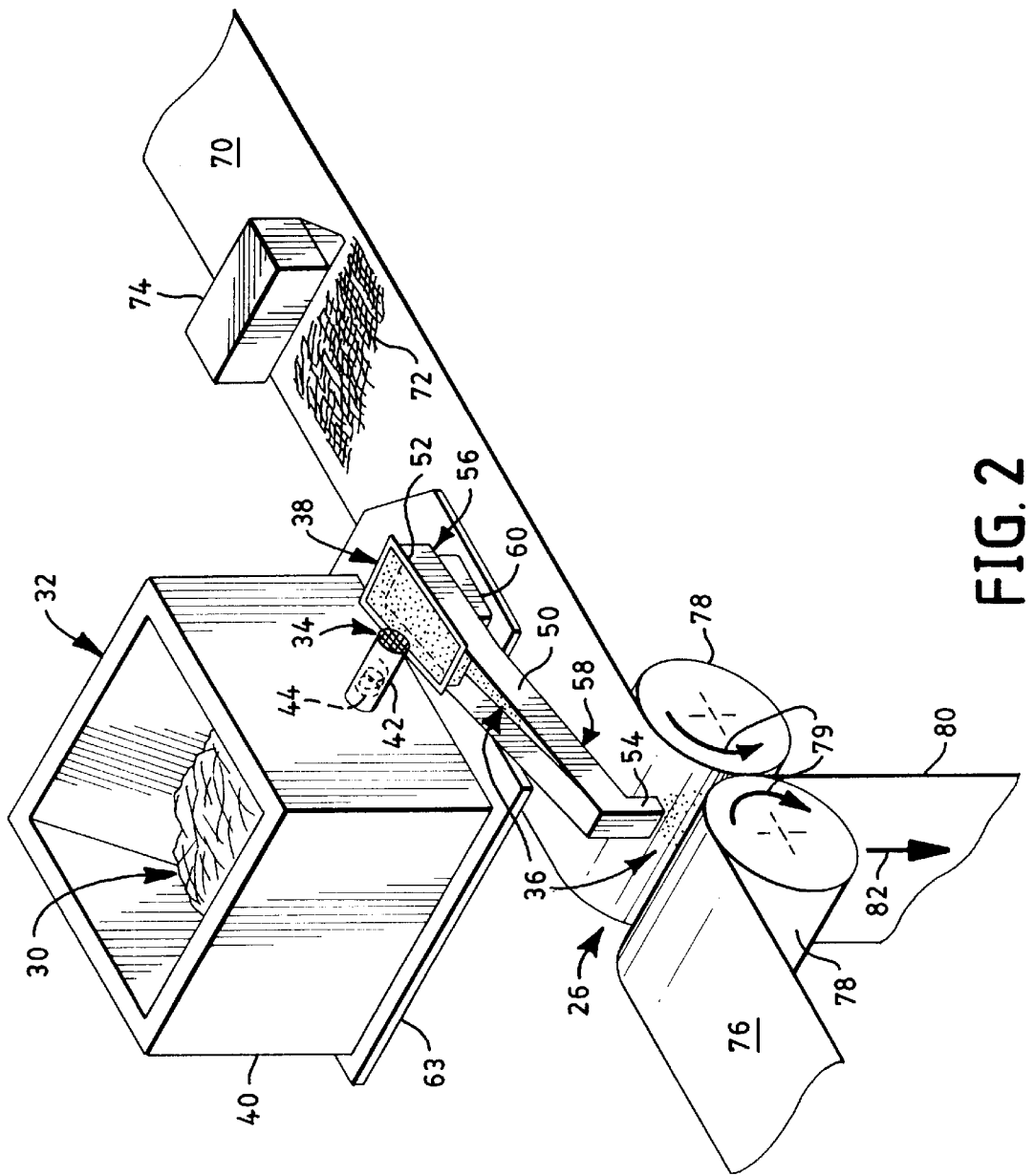
FIG. 2 representatively shows a perspective view of equipment used in one embodiment of the method for processing zeolite, such as molecular sieve, powders.

In one embodiment, the method for distributing a zeolite powder 30 may be carried out using the equipment illustrated in FIG. 2. In general, the method utilizes a metering device 32 that receives the zeolite powder 30 from a source 20 (FIG. 1) and delivers it to an extrusion device 34. The extrusion device 34 separates the powder 30 into generally uniform diameter particulate material 36 including clusters and individual particles that are then delivered to a vibration device 38. The vibration device 38 is operable to further separate the clusters into smaller sizes and deliver the powder to a deposition station 26 for incorporation into a product.

The illustrated metering device 32 comprises a volumetric feeder including a bulk solids agitating hopper 40, a nozzle 42, and a rotating helix (screw) 44 that extends at least partially into the interior of the hopper 40 and transports the zeolite powder 30 out of the hopper through the nozzle 42. The hopper 40 desirably comprises a liner (not shown) formed of rubber or the like and an agitator mechanism (not shown) to shake the liner and cause the powder 30 to drop toward the rotating helix 44. Suitable metering devices 32 are available from AccuRate Inc. of Whitewater, Wis., USA, under the trademark ACCURATE. One such system is a 604 Series volumetric feeder using dual ¼ horsepower motors for separate agitation speed control and a 1 inch square stock helix having a spiral that is open in the center to prevent powder buildup on the center shaft.

For applications involving absorbent articles, the metering device 32 may for example supply the zeolite powder 30 at a feedrate of at least 50 grams per minute, such as about 55 grams per minute. Alternative metering devices such as a weight loss feeder, a flatstock helix, an auger, or the like may also be used.

The extrusion device 34 comprises a screening mechanism such as ¹⁄₁₆ inch mesh rectangular screen (1.59 mm). Selection of a screen size should consider the desired particle size exiting the screen in combination with the metering device power and desired system throughput. This screen desirably provides a generally uniform diameter powder particulate size. Upon exiting the extrusion device 34, the particulate material 36 desirably has a generally uniform average diameter of less than about 1500 microns, and particularly less than about 1100 microns, for improved performance. It may be beneficial to intentionally agglomerate the zeolite particles into generally uniform diameter clusters by extrusion or other means in order to improve the overall uniformity and distribution of clusters at the deposition station 26.

Other mechanisms such as a sifter or the like may alternatively be used to refine the zeolite powder 30 into appropriately sized particulate material 36. From the screen, the clusters and individual particles 36 fall by gravity or are transported by other suitable means to the vibration device 38.

In the illustrated embodiment, the vibration device 36 comprises a vibrating horn 50, a basket 52 disposed on the vibrating horn, and a funnel 54 to direct particulate material 36 exiting the vibrating horn 50. The vibrating horn 50 has opposite entry and exit ends 56 and 58 between which particulate material 36 travels prior to exiting through the optional funnel 54. In the illustrated embodiment, the vibrating horn 50 narrows from about 3 inches (7.6 cm) at the entry end 56 to about 1.5 inch (3.8 cm) at the entrance to the funnel 54. The hopper 40 and the vibrating horn 50 are both mounted on a frame 63 which is connected to a fixed structural support (not shown). The funnel 54 is used to control the direction of the particulate material 36.

The basket 52 is mounted at the entry end 56 of the vibrating horn 50 so that particulate material 36 exiting the extrusion device 34 is deposited in the basket 52. The basket 52 is desirably formed of a perforated material such as metal or the like. The basket 52 functions to accumulate particulate material 36 and eliminate surges of material; widen the distribution pattern of the particulate material; and sift the particulate material through the perforations onto the vibrating horn 50 to evenly distribute the particulate material 36 across the width of the basket 52.

The vibrating horn 50 comprises an actuator 60 that is operably connected to a power source (not shown) and adapted to vibrate the horn. One suitable actuator 60 is a 20 watt vibrator operating at 3600 cycles per minute. The design of the horn 50 and the operating characteristics of the actuator 60 are selected so that the particulate material 36 is transported through the basket 52 and to the exit end 58 of the vibrating horn.

At the deposition station 26, the particulate material 36 exits the funnel 54 and is deposited onto a substantially continuous moving carrier substrate 70. In an alternative embodiment, the particulate material 36, at the deposition station 26, is deposited onto a substantially continuous moving carrier, including but not limited to machinery such as screens, belts, and vibrating horns. Optionally, an adhesive 72 is deposited onto the carrier substrate 70 by an adhesive die head 74, either prior to or after placement of the particulate material 36 on the carrier substrate. Also optionally, a substantially continuous, moving cover substrate 76 may be married with the carrier substrate 70 at nip rolls 78 rotating in the direction of arrows 79 to sandwich the particulate material 36 between the carrier and cover substrates. The carrier and cover substrates 70 and 76 suitably comprise gas permeable materials such as nonwovens or apertured films. In one particular embodiment the substrates 70 and 76 comprise cellulosic tissue wraps each having a basis weight of 26 grams per square meter (gsm).

The adhesive 72 functions to bond the particulate material 36 and the cover substrate 76 to the carrier substrate 70, thus forming a composite 80 moving in the direction of arrow 82. The adhesive 72 is desirably applied in a meltspray application that bonds the zeolite particles in place but does not block volatile materials from reaching the crystalline structure of the zeolite. One suitable adhesive die unit for dispensing the adhesive is available from J and M Laboratories, Inc. of Dawsonville, Ga., USA, and is identified as a MAMBI DURAFIBER die, Model DF-12-16. The particular adhesive 72 is desirably a hot melt adhesive that does not significantly contaminate the efficacy of the zeolite. Suitable adhesives are available from Ato Findley Adhesives from Wauwatosa, Wis., USA, under the trade designation H-2088 or National Starch and Chemical Corporation of Bridgewater, N.J., USA, under the trade designation 34-5610.

In particular embodiments, the carrier and cover substrates 70 and 76 may be transported at speeds of over 300 feet per minute (fpm), for example about 333 fpm. Further, the resultant composite 80 may include zeolite add-on levels of about 0.1 to about 50 gsm with hot melt adhesive add-on levels of about 3 to about 10 gsm. More particularly, the zeolite add-on level may range between about 4 to about 50 gsm. Suitable adhesion of the zeolite to the substrates and the substrates to one another is believed possible at about 3 to about 5 gsm melt spray add-ons. The wide ranges of zeolite and adhesive add-ons yield a large matrix of odor controlling material composites 80 that are capable of being incorporated into personal care absorbent articles or other products.

Figure 3:
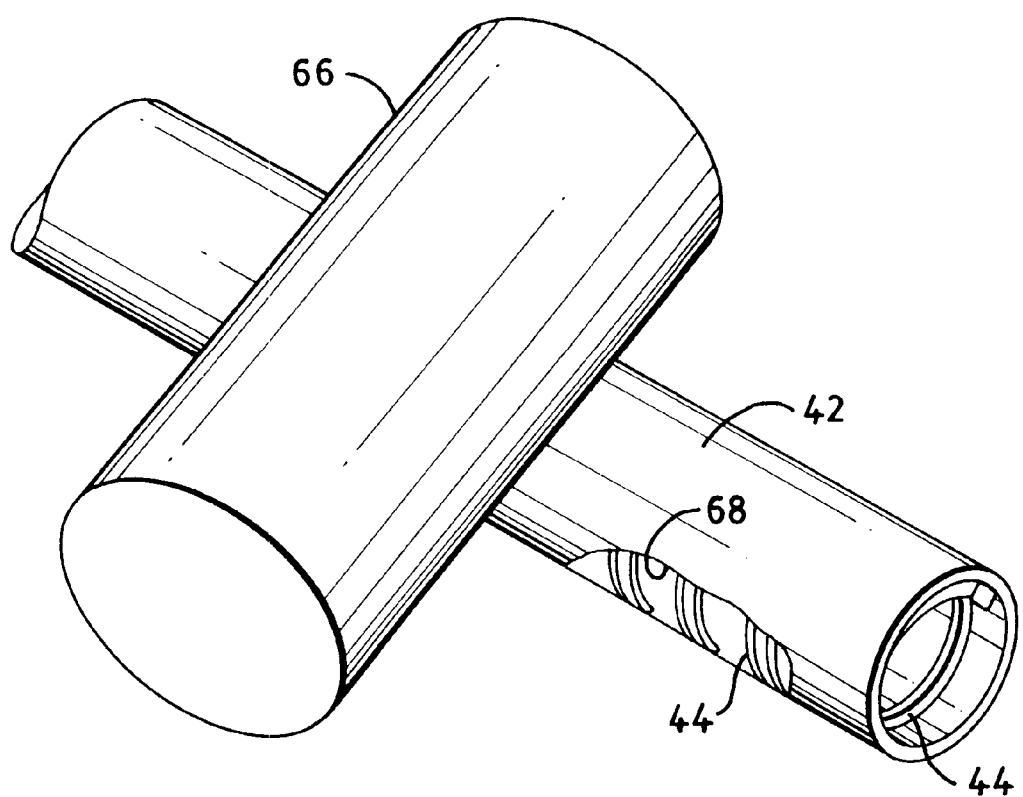
FIG. 3 representatively shows an enlarged perspective view of alternative equipment used in the method for processing zeolite, such as molecular sieve, powders.

Alternative refining equipment is illustrated in FIG. 3. Similar to the equipment of FIG. 2, the zeolite powder 30 is processed through a metering device 32 (not shown) having a nozzle 42 and a rotating helix 44. Rather than the extrusion device 34 and vibrating horn 50, though, in this embodiment refining is accomplished by vibrating the nozzle 42 and causing the particulate material 36 (not shown) to be distributed through a slot 68 in the nozzle. In particular, a vibration device 66 is operably connected to a power source (not shown) and adapted to vibrate the nozzle 42. The size of the slot 68 may be selected to provide the desired spreading pattern, and may be adjustable. In one particular embodiment, the slot 68 has a length of about 1.5 inches (3.81 cm) and a height of 0.375 inch (0.95 cm). The particulate material 36 exiting the slot 68 desirably have mean diameters of the same magnitude as referenced above in relation to the extrusion device of FIG. 2.

Figure 4:
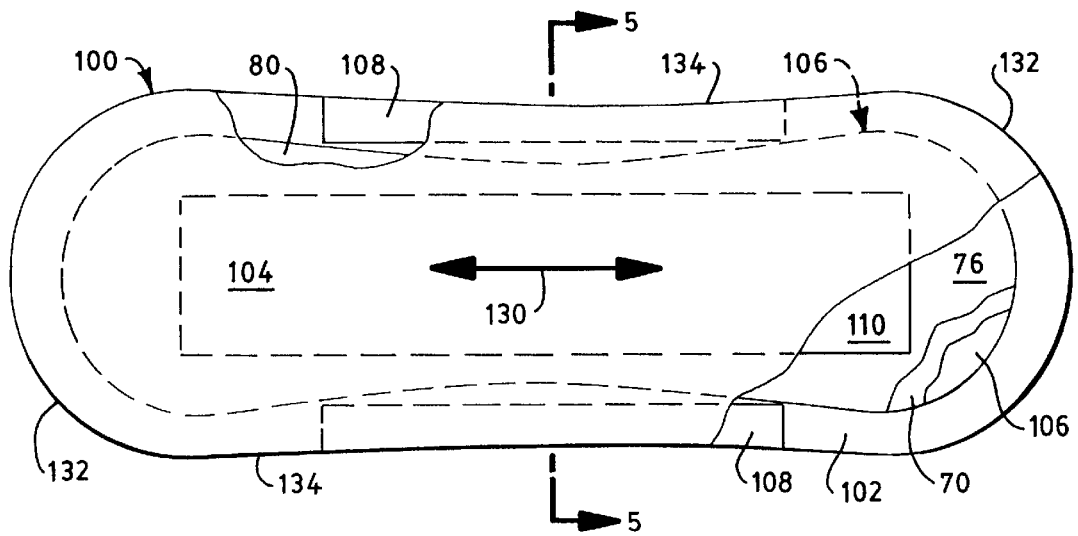
FIG. 4 representatively shows an absorbent article containing zeolite, such as molecular sieve, particles that have been distributed according to the present method.
Figure 5:
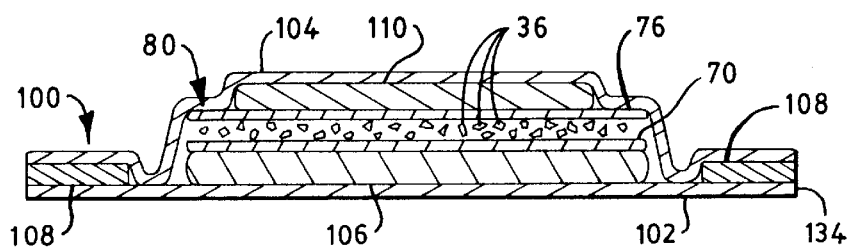
FIG. 5 representatively shows a section view taken generally from the plane of the line 5—5 in FIG. 4.

By way of illustration, one exemplary absorbent article utilizing a zeolite composite 80 is illustrated by an incontinence pad 100 in FIGS. 4 and 5. The pad 100 includes a moisture barrier 102, a bodyside liner 104, a retention portion in the form of an absorbent assembly 106 disposed between the moisture barrier and bodyside liner, and a molecular sieve composite 80 disposed between the absorbent assembly and the bodyside liner. Desirably although not necessarily, the pad 100 may also include side elastic members 108 and a liquid acquisition/distribution layer 110. The pad 100 desirably further comprises a means for holding the pad 100 in position during use (not shown). For example, the pad 100 may comprise a garment attachment adhesive, a body attachment adhesive, belts, straps, wings, mechanical fasteners, and/or other suitable fastening devices to secure the pad in position to absorb body exudates.

With particular reference to FIG. 4, the illustrated pad 100 defines a longitudinal axis or center line represented by arrow 130, which generally corresponds to the greatest planar dimension of the product. The pad 100 has opposite, longitudinal end edges 132 and opposite, longitudinal side edges 134 that extend between the longitudinal end edges. The longitudinal side edges 134 are shown as generally straight, but optionally, may be curvilinear and contoured, for example so that the pad 100 is generally hourglass shaped.

The moisture barrier 102 and bodyside liner 104 are desirably longer and wider than the absorbent assembly 106 and the composite 80 so that the peripheries of the moisture barrier and bodyside liner may be bonded together using ultrasonic bonds, thermal bonds, adhesives, or other suitable means. Additionally, the absorbent assembly 106 and the composite 80 may be bonded directly to the moisture barrier 102 and the bodyside liner 104 using ultrasonic bonds, thermal bonds, adhesives, or other suitable means. As used herein, the term "bonded" refers to the joining, adhering, connecting, attaching, or the like, of two elements. Two elements will be considered to be bonded together when they are bonded directly to one another or indirectly to one another, such as when each is directly bonded to intermediate elements.

The moisture barrier or backsheet 102 desirably comprises a material that is formed or treated to be liquid impermeable. Alternatively, the moisture barrier 102 may comprise a liquid permeable material and other suitable means may be provided to impede liquid movement away from the absorbent assembly 106, such as a liquid impermeable layer (not shown) associated with the absorbent assembly. The moisture barrier 102 may also be gas permeable over either all or part of its surface area.

The moisture barrier 102 may comprise a single layer of material or a laminate of two or more separate layers of material. Suitable moisture barrier materials include films, wovens, nonwovens, laminates of films, wovens, and/or nonwovens, or the like. For example, the moisture barrier 102 may comprise a thin, substantially liquid impermeable web or sheet of plastic film such as polyethylene, polypropylene, polyvinyl chloride or similar material. The moisture barrier material may be transparent or opaque and have an embossed or matte surface. One particular material for the moisture barrier 102 is a polyethylene film that has a nominal thickness of about 0.028 millimeter and a systematic matte embossed pattern, and that has been corona treated on both sides.

The absorbent assembly 106 comprises materials adapted to absorb, distribute, and retain liquid waste, and may be in the form of a single or multi-layered structure. The absorbent assembly 106 may comprise various absorbent materials, such as an air-formed batt of cellulosic fibers (i.e., wood pulp fluff) or a coform material composed of a mixture of cellulosic fibers and synthetic polymer fibers. The absorbent assembly 106 may include 0–95 weight percent of organic or inorganic high-absorbency materials to increase the absorbency of the assembly. As used herein, the term "high-absorbency materials" refers to materials that are capable of absorbing at least about 15 and desirably more than 25 times their weight in water. Suitable high-absorbency materials are described in U.S. Pat. Nos. 4,699,823 issued Oct. 13, 1987, to Kellenberger et al. and 5,147,343 issued Sep. 15, 1992, to Kellenberger, which are incorporated herein by reference. High-absorbency materials are available from various commercial vendors, such as The Dow Chemical Company; Hoechst Celanese Corporation; Chemische Fabrik Stockhausen, GMBH; and Allied Colloids, Inc.

The zeolite composite 80 is shown in particularly large scale in order to illustrate the presence of the molecular sieve particulate material 36. The composite 80 may be cut or trimmed as needed along with the absorbent assembly 106, for example to provide the hourglass shaped structure as illustrated in FIGS. 4 and 5. Alternatively, the composite 80 may be sized to reside within the pad 100 without being trimmed during assembly of the pad 100.

The acquisition/distribution layer 110 is desirably provided to help decelerate and diffuse surges of liquid that may be introduced into the absorbent assembly 106. The acquisition/distribution layer 110 may be positioned subjacent the bodyside liner 104 as illustrated, or alternatively disposed on the inwardly facing, bodyside surface of bodyside liner. Suitable configurations of the acquisition/distribution layer 110 are described in U.S. Pat. No. 5,192,606 issued Mar. 9, 1993, to D. Proxmire et al.; U.S. Pat. No. 5,486,166 issued Jan. 23, 1996 to Ellis et al.; U.S. Pat. No. 5,490,846 issued Feb. 13, 1996 to Ellis et al.; and U.S. patent application Ser. No. 096,654 of W. Hanson et al., titled "Thin Absorbent Article Having Rapid Uptake Of Liquid," and filed Jul. 22, 1993 now U.S. Pat. No. 5,509,915; the disclosures of which are hereby incorporated by reference. By way of illustration, the acquisition/distribution layer 110 may comprise a through-air bonded carded web composed of a blend of 40% of 6 denier polyester fibers, commercially available from Hoechst Celanese Corporation, and 60% of 3 denier polypropylene/polyethylene side-by-side bicomponent fibers, commercially available from BASF Corporation, and have an overall basis weight of from about 50 to about 120 gsm.

The bodyside liner or topsheet 104 is formed of a liquid permeable material so that liquid waste, and possibly semi-solid waste as well, can pass through the liner and be absorbed by the absorbent assembly 106. Suitable bodyside liners 104 may comprise a nonwoven web or sheet of wet strength tissue paper, an apertured film, a spunbonded, meltblown or bonded-carded web composed of synthetic polymer filaments or fibers, such as polypropylene, polyethylene, polyesters or the like, or a web of natural polymer filaments or fibers such as rayon or cotton. In addition, the bodyside liner 104 may be treated with a surfactant to aid in liquid transfer. In one particular embodiment, the liner 104 comprises a nonwoven, spunbond polypropylene fabric having a basis weight of about 17 gsm. The fabric is pin apertured and surface treated with a surfactant commercially available from Union Carbide Chemicals and Plastics Company, Inc. under the trade designation TRITON X-102. As used herein, the term "fabric" is used to refer to all of the woven, knitted and nonwoven fibrous webs. The term "nonwoven web" means a web of material that is formed without the aid of a textile weaving or knitting process.

In the illustrated embodiment, the elongated side elastic members 108 are longitudinally orientated contiguous with each side edge 134 and extend toward the end edges 132. The side elastic members 108 may be bonded in a stretched condition intermediate the moisture barrier 102 and the bodyside liner 104 using ultrasonic bonds, adhesives, thermal bonds, or other suitable means, in either a straight or a curved shape. Alternatively, the side elastic members 108 may be bonded in a relaxed state to a gathered portion of the moisture barrier 102, the bodyside liner 104, or both. As used herein, the terms "elastic", "elasticized" and "elasticity" mean that property of a material by virtue of which it tends to recover its original size and shape after removal of a force causing a deformation.

The side elastic members 108 may be formed of a dry-spun coalesced multifilament elastomeric thread sold under the tradename LYCRA and available from E. I. Du Pont de Nemours and Company. Alternately, the elastic members may be formed of other typical elastics utilized in making incontinence products, such as a thin ribbon of natural rubber, a stretch bonded laminate material comprising a prestretched elastic meltblown inner layer sandwiched between and bonded to a pair of spunbond polypropylene nonwoven webs, or the like. Elasticity could also be imparted to the absorbent article by extruding a hot melt elastomeric adhesive between the moisture barrier 102 and the liner 104. Other suitable elastic gathering means are disclosed in U.S. Pat. Nos. 4,938,754 to Mesek and 4,388,075 to Mesek et al.

The powder may desirably comprise individual molecular sieve particles having a median particle size of less than 350 microns, particularly less than about 200 microns, more particularly less than about 100 microns, and most particularly less than about 50 microns. In one particular embodiment, the molecular sieve has a particle size distribution from 1.4 to 44 microns with a median particle size of about 3.7 microns. One suitable procedure for determining the particle size of a molecular sieve is a standard sieve analysis, although other techniques such as optical microscopy, image analysis, optical or resistivity zone sensing, or the like may also be appropriate depending upon the general size of the particles. The procedure for measuring particle size takes into consideration individual molecular sieve particles or agglomerates of such particles.

Applicants have discovered that improved handling and distribution of molecular sieve particles is possible when the moisture content is controlled to relatively high levels. By controlling the moisture content of the molecular sieve particles to the indicated levels, the powder becomes conductive and thus discharges most of its static charge. This can be visually observed by a reduction in the occurrence of sparks that would otherwise be present, and by less movement of the particles as a consequence of objects, such as a person's hand, moving in close proximity to the particles. The reduced static levels diminish the propensity of the molecular sieve particles to form clusters and limit the integrity of the clusters to levels at which separation, for example by mechanical means, is economically feasible. More specifically, the powder can be separated into a finer and more uniform final particulate. This improved molecular sieve distribution permits a cost effective utilization of the odor control material because the finer distribution provides better odor adsorption performance. From a processing standpoint, the reduced levels of static also lessen airborne contamination, referred to as dusting; decrease buildup of the material on working surfaces; and permit easier removal of any such buildups by airjets or vacuum.

In one embodiment, the method for distributing a molecular sieve powder 30 may be carried out using the equipment illustrated in FIG. 2. In general, the method utilizes a metering device 32 that receives the molecular sieve powder 30 from a source 20 (FIG. 1) and delivers it to an extrusion device 34. The extrusion device 34 separates the powder 30 into generally uniform diameter particulate material 36 including clusters and individual particles that are then delivered to a vibration device 38. The vibration device 38 is operable to further separate the clusters into smaller sizes and deliver the powder to a deposition station 26 for incorporation into a product.

The illustrated metering device 32 comprises a volumetric feeder including a bulk solids agitating hopper 40, a nozzle 42, and a rotating helix (screw) 44 that extends at least partially into the interior of the hopper 40 and transports the molecular sieve powder 30 out of the hopper through the nozzle 42. The hopper 40 desirably comprises a liner (not shown) formed of rubber or the like and an agitator mechanism (not shown) to shake the liner and cause the powder 30 to drop toward the rotating helix 44. Suitable metering devices 32 are available from AccuRate Inc. of Whitewater, Wis., USA, under the trademark ACCURATE. One such system is a 604 Series volumetric feeder using dual ¼ horsepower motors for separate agitation speed control and a 1 inch square stock helix having a spiral that is open in the center to prevent powder buildup on the center shaft.

For applications involving absorbent articles, the metering device 32 may for example supply the molecular sieve powder 30 at a feedrate of at least 50 grams per minute, such as about 55 grams per minute. Alternative metering devices such as a weight loss feeder, a flatstock helix, an auger, or the like may also be used.

The extrusion device 34 comprises a screening mechanism such as 1/16 inch mesh rectangular screen (1.59 mm). Selection of a screen size should consider the desired particle size exiting the screen in combination with the metering device power and desired system throughput. This screen desirably provides a generally uniform diameter powder particulate size. Upon exiting the extrusion device 34, the particulate material 36 desirably has a generally uniform average diameter of less than about 1500 microns, and particularly less than about 1100 microns, for improved performance. It may be beneficial to intentionally agglomerate the molecular sieve particles into generally uniform diameter clusters by extrusion or other means in order to improve the overall uniformity and distribution of clusters at the deposition station 26.

Other mechanisms such as a sifter or the like may alternatively be used to refine the molecular sieve powder 30 into appropriately sized particulate material 36. From the screen, the clusters and individual particles 36 fall by gravity or are transported by other suitable means to the vibration device 38.

In the illustrated embodiment, the vibration device 36 comprises a vibrating horn 50, a basket 52 disposed on the vibrating horn 50, and a funnel 54 to direct particulate material 36 exiting the vibrating horn 50. The vibrating horn 50 has opposite entry and exit ends 56 and 58 between which particulate material 36 travels prior to exiting through the optional funnel 54. In the illustrated embodiment, the vibrating horn 50 narrows from about 3 inches (7.6 cm) at the entry end 56 to about 1.5 inch (3.8 cm) at the entrance to the funnel 54. The hopper 40 and the vibrating horn 50 are both mounted on a frame 63 which is connected to a fixed structural support (not shown). The funnel 54 is used to control the direction of the particulate material 36.

The basket 52 is mounted at the entry end 56 of the vibrating horn 50 so that particulate material 36 exiting the extrusion device 34 is deposited in the basket 52. The basket 52 is desirably formed of a perforated material such as metal or the like. The basket 52 functions to accumulate particulate material 36 and eliminate surges of material; widen the distribution pattern of the particulate material 36; and sift the particulate material 36 through the perforations onto the vibrating horn 50 to evenly distribute the particulate material 36 across the width of the basket 52.

The vibrating horn 50 comprises an actuator 60 that is operably connected to a power source (not shown) and adapted to vibrate the horn 50. One suitable actuator 60 is a 20 watt vibrator operating at 3600 cycles per minute. The design of the horn 50 and the operating characteristics of the actuator 60 are selected so that the particulate material 36 is transported through the basket 52 and to the exit end 58 of the vibrating horn 50.

At the deposition station 26, the particulate material 36 exits the funnel 54 and is deposited onto a substantially continuous moving carrier substrate 70. In an alternative embodiment, the particulate material 36, at the deposition station 26, is deposited onto a substantially continuous moving carrier, including but not limited to machinery such as screens, belts, and vibrating horns. Optionally, an adhesive 72 is deposited onto the carrier substrate 70 by an adhesive die head 74, either prior to or after placement of the particulate material 36 on the carrier substrate. Also optionally, a substantially continuous, moving cover substrate 76 may be married with the carrier substrate 70 at nip rolls 78 rotating in the direction of arrows 79 to sandwich the particulate material 36 between the carrier and cover substrates. The carrier and cover substrates 70 and 76 suitably comprise gas permeable materials such as nonwovens or apertured films. In one particular embodiment the substrates 70 and 76 comprise cellulosic tissue wraps each having a basis weight of 26 grams per square meter (gsm).

The adhesive 72 functions to bond the particulate material 36 and the cover substrate 76 to the carrier substrate 70, thus forming a composite 80 moving in the direction of arrow 82. The adhesive 72 is desirably applied in a meltspray application that bonds the molecular sieve particles in place but does not block volatile materials from reaching the crystalline structure of the molecular sieve. One suitable adhesive die unit for dispensing the adhesive is available from J and M Laboratories, Inc. of Dawsonville, Ga., USA, and is identified as a MAMBI DURAFIBER die, Model DF-12-16. The particular adhesive 72 is desirably a hot melt adhesive that does not significantly contaminate the efficacy of the molecular sieve. Suitable adhesives are available from Ato Findley Adhesives from Wauwatosa, Wis., USA, under the trade designation H-2088 or National Starch and Chemical Corporation of Bridgewater, N.J., USA, under the trade designation 34-5610.

In particular embodiments, the carrier and cover substrates 70 and 76 may be transported at speeds of over 300 feet per minute (fpm), for example about 333 fpm. Further, the resultant composite 80 may include molecular sieve add-on levels of about 0.1 to about 50 gsm with hot melt adhesive add-on levels of about 3 to about 10 gsm. More particularly, the molecular sieve add-on level may range between about 4 to about 50 gsm. Suitable adhesion of the molecular sieve to the substrates and the substrates to one another is believed possible at about 3 to about 5 gsm melt spray add-ons. The wide ranges of molecular sieve and adhesive add-ons yield a large matrix of odor controlling material composites 80 that are capable of being incorporated into personal care absorbent articles or other products.

Alternative refining equipment is illustrated in FIG. 3. Similar to the equipment of FIG. 2, the molecular sieve powder 30 is processed through a metering device 32 (not shown) having a nozzle 42 and a rotating helix 44. Rather than the extrusion device 34 and vibrating horn 50, though, in this embodiment refining is accomplished by vibrating the nozzle 42 and causing the particulate material 36 (not shown) to be distributed through a slot 68 in the nozzle. In particular, a vibration device 66 is operably connected to a power source (not shown) and adapted to vibrate the nozzle 42. The size of the slot 68 may be selected to provide the desired spreading pattern, and may be adjustable. In one particular embodiment, the slot 68 has a length of about 1.5 inches (3.81 cm) and a height of 0.375 inch (0.95 cm). The particulate material 36 exiting the slot 68 desirably have mean diameters of the same magnitude as referenced above in relation to the extrusion device of FIG. 2.

By way of illustration, one exemplary absorbent article utilizing a molecular sieve composite 80 is illustrated by an incontinence pad 100 in FIGS. 4 and 5. The pad 100 includes a moisture barrier 102, a bodyside liner 104, a retention portion in the form of an absorbent assembly 106 disposed between the moisture barrier and bodyside liner, and a molecular sieve composite 80 disposed between the absorbent assembly 106 and the bodyside liner 104. Desirably although not necessarily, the pad 100 may also include side elastic members 108 and a liquid acquisition/distribution layer 110. The pad 100 desirably further comprises a means for holding the pad 100 in position during use (not shown). For example, the pad 100 may comprise a garment attachment adhesive, a body attachment adhesive, belts, straps, wings, mechanical fasteners, and/or other suitable fastening devices to secure the pad in position to absorb body exudates.

With particular reference to FIG. 4, the illustrated pad 100 defines a longitudinal axis or center line represented by arrow 130, which generally corresponds to the greatest planar dimension of the product. The pad 100 has opposite, longitudinal end edges 132 and opposite, longitudinal side edges 134 that extend between the longitudinal end edges. The longitudinal side edges 134 are shown as generally straight, but optionally, may be curvilinear and contoured, for example so that the pad 100 is generally hourglass shaped.

The moisture barrier 102 and bodyside liner 104 are desirably longer and wider than the absorbent assembly 106 and the composite 80 so that the peripheries of the moisture barrier 102 and bodyside liner 104 may be bonded together using ultrasonic bonds, thermal bonds, adhesives, or other suitable means. Additionally, the absorbent assembly 106 and the composite 80 may be bonded directly to the moisture barrier 102 and the bodyside liner 104 using ultrasonic bonds, thermal bonds, adhesives, or other suitable means. As used herein, the term "bonded" refers to the joining, adhering, connecting, attaching, or the like, of two elements. Two elements will be considered to be bonded together when they are bonded directly to one another or indirectly to one another, such as when each is directly bonded to intermediate elements.

The moisture barrier or backsheet 102 desirably comprises a material that is formed or treated to be liquid impermeable. Alternatively, the moisture barrier 102 may comprise a liquid permeable material and other suitable means may be provided to impede liquid movement away from the absorbent assembly 106, such as a liquid impermeable layer (not shown) associated with the absorbent assembly. The moisture barrier 102 may also be gas permeable over either all or part of its surface area.

The moisture barrier 102 may comprise a single layer of material or a laminate of two or more separate layers of material. Suitable moisture barrier materials include films, wovens, nonwovens, laminates of films, wovens, and/or nonwovens, or the like. For example, the moisture barrier 102 may comprise a thin, substantially liquid impermeable web or sheet of plastic film such as polyethylene, polypropylene, polyvinyl chloride or similar material. The moisture barrier material may be transparent or opaque and have an embossed or matte surface. One particular material for the moisture barrier 102 is a polyethylene film that has a nominal thickness of about 0.028 millimeter and a systematic matte embossed pattern, and that has been corona treated on both sides.

The absorbent assembly 106 comprises materials adapted to absorb, distribute, and retain liquid waste, and may be in the form of a single or multi-layered structure. The absorbent assembly 106 may comprise various absorbent materials, such as an air-formed batt of cellulosic fibers (i.e., wood pulp fluff) or a coform material composed of a mixture of cellulosic fibers and synthetic polymer fibers. The absorbent assembly 106 may include 0–95 weight percent of organic or inorganic high-absorbency materials to increase the absorbency of the assembly. As used herein, the term "high-absorbency materials" refers to materials that are capable of absorbing at least about 15 and desirably more than 25 times their weight in water. Suitable high-absorbency materials are described in U.S. Pat. Nos. 4,699,823 issued Oct. 13, 1987, to Kellenberger et al. and 5,147,343 issued Sep. 15, 1992, to Kellenberger, which are incorporated herein by reference. High-absorbency materials are available from various commercial vendors, such as The Dow Chemical Company; Hoechst Celanese Corporation; Chemische Fabrik Stockhausen, GMBH; and Allied Colloids, Inc.

The molecular sieve composite 80 is shown in particularly large scale in order to illustrate the presence of the molecular sieve particulate material 36. The composite 80 may be cut or trimmed as needed along with the absorbent assembly 106, for example to provide the hourglass shaped structure as illustrated in FIGS. 4 and 5. Alternatively, the composite 80 may be sized to reside within the pad 100 without being trimmed during assembly of the pad 100.

The acquisition/distribution layer 110 is desirably provided to help decelerate and diffuse surges of liquid that may be introduced into the absorbent assembly 106. The acquisition/distribution layer 110 may be positioned subjacent the bodyside liner 104 as illustrated, or alternatively disposed on the inwardly facing, bodyside surface of bodyside liner. Suitable configurations of the acquisition/distribution layer 110 are described in U.S. Pat. No. 5,192,606 issued Mar. 9, 1993, to D. Proxmire et al.; U.S. Pat. No. 5,486,166 issued Jan. 23, 1996 to Ellis et al.; U.S. Pat. No. 5,490,846 issued Feb. 13, 1996 to Ellis et al.; and U.S. patent application Ser. No. 096,654 of W. Hanson et al., titled "Thin Absorbent Article Having Rapid Uptake Of Liquid," and filed Jul. 22, 1993 now U.S. Pat. No. 5,509,915; the disclosures of which are hereby incorporated by reference. By way of illustration, the acquisition/distribution layer 110 may comprise a through-air bonded carded web composed of a blend of 40% of 6 denier polyester fibers, commercially available from Hoechst Celanese Corporation, and 60% of 3 denier polypropylene/polyethylene side-by-side bicomponent fibers, commercially available from BASF Corporation, and have an overall basis weight of from about 50 to about 120 gsm.

The bodyside liner or topsheet 104 is formed of a liquid permeable material so that liquid waste, and possibly semi-solid waste as well, can pass through the liner and be absorbed by the absorbent assembly 106. Suitable bodyside liners 104 may comprise a nonwoven web or sheet of wet strength tissue paper, an apertured film, a spunbonded, meltblown or bonded-carded web composed of synthetic polymer filaments or fibers, such as polypropylene, polyethylene, polyesters or the like, or a web of natural polymer filaments or fibers such as rayon or cotton. In addition, the bodyside liner 104 may be treated with a surfactant to aid in liquid transfer. In one particular embodiment, the liner 104 comprises a nonwoven, spunbond polypropylene fabric having a basis weight of about 17 gsm. The fabric is pin apertured and surface treated with a surfactant commercially available from Union Carbide Chemicals and Plastics Company, Inc. under the trade designation TRITON X-102. As used herein, the term "fabric" is used to refer to all of the woven, knitted and nonwoven fibrous webs. The term "nonwoven web" means a web of material that is formed without the aid of a textile weaving or knitting process.

In the illustrated embodiment, the elongated side elastic members 108 are longitudinally orientated contiguous with each side edge 134 and extend toward the end edges 132. The side elastic members 108 may be bonded in a stretched condition intermediate the moisture barrier 102 and the bodyside liner 104 using ultrasonic bonds, adhesives, thermal bonds, or other suitable means, in either a straight or a curved shape. Alternatively, the side elastic members 108 may be bonded in a relaxed state to a gathered portion of the moisture barrier 102, the bodyside liner 104, or both. As used herein, the terms "elastic", "elasticized" and "elasticity" mean that property of a material by virtue of which it tends to recover its original size and shape after removal of a force causing a deformation.

The side elastic members 108 may be formed of a dry-spun coalesced multifilament elastomeric thread sold under the tradename LYCRA and available from E. I. Du Pont de Nemours and Company. Alternately, the elastic members may be formed of other typical elastics utilized in making incontinence products, such as a thin ribbon of natural rubber, a stretch bonded laminate material comprising a prestretched elastic meltblown inner layer sandwiched between and bonded to a pair of spunbond polypropylene nonwoven webs, or the like. Elasticity could also be imparted to the absorbent article by extruding a hot melt elastomeric adhesive between the moisture barrier 102 and the liner 104. Other suitable elastic gathering means are disclosed in U.S. Pat. Nos. 4,938,754 to Mesek and 4,388,075 to Mesek et al.

The foregoing detailed description has been for the purpose of illustration. Thus, a number of modifications and changes may be made without departing from the spirit of the scope of the present invention. For instance, alternative or optional features described as part of one embodiment can be used to yield another embodiment. Additionally, two named components could represent portions of the same structure. Therefore, the invention should not be limited by the specific embodiments described, but only by the claims.

We claim:

1. A method for distributing a zeolite powder, comprising:
   providing a powder comprising clusters of zeolite particles, the zeolite particles having a median particle size of less than about 350 microns;
   controlling the moisture content of the zeolite particles to greater than about 3 percent; and
   thereafter refining the powder to reduce the size of the clusters wherein refining comprises vibrating the powder.

2. The method of claim 1, wherein vibrating comprises sifting the powder through a perforated surface.

3. The method of claim 1, wherein the moisture content is controlled to greater than about 7 percent.

4. The method of claim 1, wherein the moisture content is controlled to between about 8 and about 10 percent.

5. The method of claim 1, 3 or 4, further comprising adding moisture to the zeolite powder to elevate the moisture content.

6. The method of claim 1, 3 or 4, wherein the zeolite particles have a median particle size of less than about 100 microns.

7. The method of claim 6, wherein the zeolite particles have a median particle size of less than about 50 microns.

8. The method of claim 1, 3 or 4, wherein refining reduces the size of the clusters to a mean diameter of less than about 1500 microns.

9. The method of claim 1, 3 or 4, wherein refining reduces the size of the clusters to a mean diameter of less than about 1100 microns.

10. The method of claim 1, 3 or 4, further comprising distributing the powder onto a carrier substrate.

11. The method of claim 10, further comprising marrying the carrier substrate with a cover substrate to sandwich the powder between the carrier and cover substrates.

12. The method of claim 11, wherein the carrier and cover substrates comprise gas permeable materials.

13. The method of claim 10, further comprising applying adhesive to the carrier substrate.

14. A method for distributing a molecular sieve powder, comprising:
   providing a powder comprising clusters of molecular sieve particles, the molecular sieve particles having a median particle size of less than about 350 microns;
   controlling the moisture content of the molecular sieve particles to greater than about 3 percent; and
   thereafter refining the powder to reduce the size of the clusters wherein refining comprises vibrating the powder.

15. The method of claim 14, wherein vibrating comprises sifting the powder through a perforated surface.

16. The method of claim 14, wherein the moisture content is controlled to greater than about 7 percent.

17. The method of claim 14, wherein the moisture content is controlled to between about 8 and about 10 percent.

18. The method of claim 14, 16, or 17, further comprising adding moisture to the molecular sieve powder to elevate the moisture content.

19. The method of claim 14, 16, or 17, wherein the molecular sieve particles have a median particle size of less than about 100 microns.

20. The method of claim 19, wherein the molecular sieve particles have a median particle size of less than about 50 microns.

21. The method of claim 14, 16, or 17, wherein refining reduces the size of the clusters to a mean diameter of less than about 1500 microns.

22. The method of claim 14, 16, or 17, wherein refining reduces the size of the clusters to a mean diameter of less than about 1100 microns.

23. The method of claim 14, 16, or 17, further comprising distributing the powder onto a carrier substrate.

24. The method of claim 23, further comprising marrying the carrier substrate with a cover substrate to sandwich the powder between the carrier and cover substrates.

25. The method of claim 24, wherein the carrier and cover substrates comprise gas permeable materials.

26. The method of claim 23, further comprising applying adhesive to the carrier substrate.

27. A method for distributing a zeolite powder, comprising:
   providing a powder comprising clusters of zeolite particles, the zeolite particles having a median particle size of less than about 350 microns;
   controlling the moisture content of the zeolite particles to greater than about 3 percent; and thereafter refining the powder to reduce the size of the clusters wherein refining comprises extruding and vibrating the powder.

28. The method of claim 27, wherein refining comprises:
   screening the powder to form clusters having a mean diameter of less than 1500 microns; and
   vibrating the screened powder to further reduce the mean diameter.

29. The method of claim 27, wherein the moisture content is controlled to greater than about 7 percent.

30. The method of claim 27, wherein the moisture content is controlled to between about 8 and about 10 percent.

31. The method of claim 27, 29 or 30, further comprising adding moisture to the zeolite powder to elevate the moisture content.

32. The method of claim 27, 29 or 30, wherein the zeolite particles have a median particle size of less than about 100 microns.

33. The method of claim 32, wherein the zeolite particles have a median particle size of less than about 50 microns.

34. The method of claim 27, 29 or 30, wherein refining reduces the size of the clusters to a mean diameter of less than about 1500 microns.

35. The method of claim 27, 29 or 30, wherein refining reduces the size of the clusters to a mean diameter of less than about 1100 microns.

36. The method of claim 27, 29 or 30, further comprising distributing the powder onto a carrier substrate.

37. The method of claim 36, further comprising marrying the carrier substrate with a cover substrate to sandwich the powder between the carrier and cover substrates.

38. The method of claim 37, wherein the carrier and cover substrates comprise gas permeable materials.

39. The method of claim 36, further comprising applying adhesive to the carrier substrate.

40. A method for distributing a molecular sieve powder, comprising:
   providing a powder comprising clusters of molecular sieve particles, the molecular sieve particles having a median particle size of less than about 350 microns;
   controlling the moisture content of the molecular sieve particles to greater than about 3 percent; and
   thereafter refining the powder to reduce the size of the clusters wherein refining comprises extruding and vibrating the powder.

41. The method of claim 40, wherein refining comprises:
   screening the powder to form clusters having a mean diameter of less than 1500 microns; and
   vibrating the screened powder to further reduce the mean diameter.

42. The method of claim 40, wherein the moisture content is controlled to greater than about 7 percent.

43. The method of claim 40, wherein the moisture content is controlled to between about 8 and about 10 percent.

44. The method of claim 40, 42, or 43, further comprising adding moisture to the molecular sieve powder to elevate the moisture content.

45. The method of claim 40, 42, or 43, wherein the molecular sieve particles have a median particle size of less than about 100 microns.

46. The method of claim 45, wherein the molecular sieve particles have a median particle size of less than about 50 microns.

47. The method of claim 40, 42, or 43, wherein refining reduces the size of the clusters to a mean diameter of less than about 1500 microns.

48. The method of claim 40, 42, or 43, wherein refining reduces the size of the clusters to a mean diameter of less than about 1100 microns.

49. The method of claim 40, 42, or 43, further comprising distributing the powder onto a carrier substrate.

50. The method of claim 49, further comprising marrying the carrier substrate with a cover substrate to sandwich the powder between the carrier and cover substrates.

51. The method of claim 50, wherein the carrier and cover substrates comprise gas permeable materials.

52. The method of claim 49, further comprising applying adhesive to the carrier substrate.

53. A method for distributing a zeolite powder, comprising:
   providing a powder comprising clusters of zeolite particles, the zeolite particles having a median particle size of less than about 350 microns;
   controlling the moisture content of the zeolite particles to greater than about 3 percent;
   refining the powder to reduce the size of the clusters;
   distributing the powder onto a carrier substrate; and,
   marrying the carrier substrate with a cover substrate to sandwich the powder between the carrier and cover substrates.

54. The method of claim 53, wherein the carrier and cover substrates comprise gas permeable materials.

55. A method for distributing a molecular sieve powder, comprising:
   providing a powder comprising clusters of molecular sieve particles, the molecular sieve particles having a median particle size of less than about 350 microns;
   controlling the moisture content of the molecular sieve particles to greater than about 3 percent;
   refining the powder to reduce the size of the clusters;
   distributing the powder onto a carrier substrate; and,
   marrying the carrier substrate with a cover substrate to sandwich the powder between the carrier and cover substrates.

56. The method of claim 55, wherein the carrier and cover substrates comprise gas permeable materials.

57. A method for distributing a zeolite powder, comprising:
   providing a powder comprising clusters of zeolite particles, the zeolite particles having a median particle size of less than about 350 microns;
   controlling the moisture content of the zeolite particles to greater than about 3 percent;
   refining the powder to reduce the size of the clusters;
   distributing the powder onto a carrier substrate; and,
   applying adhesive to the carrier substrate.

58. A method for distributing a molecular sieve powder, comprising:
   providing a powder comprising clusters of molecular sieve particles, the molecular sieve particles having a median particle size of less than about 350 microns;
   controlling the moisture content of the molecular sieve particles to greater than about 3 percent;
   refining the powder to reduce the size of the clusters;
   distributing the powder onto a carrier substrate; and,
   applying adhesive to the carrier substrate.

59. A method for making an absorbent article, comprising:
   providing a powder comprising clusters of zeolite particles, the zeolite particles having a median particle size of less than about 350 microns;

controlling the moisture content of the zeolite particles to greater than about 3 percent;

thereafter refining the powder to reduce the size of the clusters;

providing a moisture barrier, a bodyside liner and an absorbent assembly;

disposing the absorbent assembly between the moisture barrier and the bodyside liner;

distributing the refined powder between the moisture barrier and the bodyside liner; and bonding the bodyside liner to the moisture barrier.

60. The method of claim 59, wherein the powder is distributed at an add-on of about 0.1 to about 50 grams per square meter.

61. The method of claim 59, wherein distributing comprises distributing the powder onto a carrier substrate and disposing the carrier substrate between the moisture barrier and the bodyside liner.

62. The method of claim 59, 60, or 61, further comprising distributing the powder onto a carrier.

63. A method for making an absorbent article, comprising:

providing a powder comprising clusters of molecular sieve particles, the molecular sieve particles having a median particle size of less than about 350 microns;

controlling the moisture content of the molecular sieve particles to greater than about 3 percent;

thereafter refining the powder to reduce the size of the clusters;

providing a moisture barrier, a bodyside liner and an absorbent assembly;

disposing the absorbent assembly between the moisture barrier and the bodyside liner;

distributing the refined powder between the moisture barrier and the bodyside liner; and bonding the bodyside liner to the moisture barrier.

64. The method of claim 63, wherein the powder is distributed at an add-on of about 0.1 to about 50 grams per square meter.

65. The method of claim 63, wherein distributing comprises distributing the powder onto a carrier substrate and disposing the carrier substrate between the moisture barrier and the bodyside liner.

66. The method of claim 63, 64, or 65, further comprising distributing the powder onto a carrier.

* * * * *